US012570767B2

(12) United States Patent
Liao et al.

(10) Patent No.: US 12,570,767 B2
(45) Date of Patent: Mar. 10, 2026

(54) SEQUENCES OF ANTI-ECTO-5'-NUCLEOTIDASE ANTIBODIES

(71) Applicant: Xintrum Pharmaceuticals, Ltd., Nanjing (CN)

(72) Inventors: Gaoyong Liao, Nanjing (CN); Haijian Ding, Nanjing (CN); Ling Wang, Nanjing (CN); Yi Zhang, Nanjing (CN)

(73) Assignee: JIANGSU KANION PHARMACEUTICAL CO., LTD., Lianyungang (CN)

(*) Notice: Subject to any disclaimer, the term of this patent is extended or adjusted under 35 U.S.C. 154(b) by 958 days.

(21) Appl. No.: 17/827,630

(22) Filed: May 27, 2022

(65) Prior Publication Data

US 2022/0356267 A1 Nov. 10, 2022

Related U.S. Application Data

(63) Continuation of application No. PCT/CN2021/131861, filed on Nov. 19, 2021.

(30) Foreign Application Priority Data

Nov. 9, 2020 (CN) ......................... 202011239238.1

(51) Int. Cl.
| | |
|---|---|
| C07K 16/28 | (2006.01) |
| A61K 39/00 | (2006.01) |
| A61P 35/00 | (2006.01) |
| C07K 16/40 | (2006.01) |

(52) U.S. Cl.
CPC .............. *C07K 16/40* (2013.01); *A61P 35/00* (2018.01); *C07K 16/2896* (2013.01); *A61K 2039/505* (2013.01); *C07K 2317/565* (2013.01); *C07K 2317/76* (2013.01); *C07K 2317/92* (2013.01)

(58) Field of Classification Search
CPC ............... A61P 35/00; C07K 16/2896; C07K 2317/76
See application file for complete search history.

(56) References Cited

U.S. PATENT DOCUMENTS

| | | | | |
|---|---|---|---|---|
| 2017/0355756 | A1* | 12/2017 | Julien | C07K 16/18 |
| 2020/0399389 | A1* | 12/2020 | Wang | C07K 16/2896 |

FOREIGN PATENT DOCUMENTS

| | | | |
|---|---|---|---|
| CN | 107001472 A | 8/2017 | |
| CN | 107001474 A | 8/2017 | |
| CN | 110785187 A | 2/2020 | |
| WO | WO-2008068048 A2 * | 6/2008 | A61P 31/10 |

OTHER PUBLICATIONS

Almagro JC, Fransson J. Humanization of antibodies. Front Biosci. Jan. 1, 2008;13:1619-33. (Year: 2008).*

Edwards et al. The remarkable flexibility of the human antibody repertoire; isolation of over one thousand different antibodies to a single protein, BLyS. J Mol Biol Nov. 14, 2003;334(1):103-18. (Year: 2003).*

International Search Report on PCT/CN2021/131861.

* cited by examiner

*Primary Examiner* — Aurora M Fontainhas
*Assistant Examiner* — Jennifer A Benavides
(74) *Attorney, Agent, or Firm* — Yong Chen; Lin Sun-Hoffman; Liu Chen & Hoffman LLP

(57) ABSTRACT

This invention involves immunizing mice with human ecto-5'-nucleotidase (CD73) to obtain multiple monoclonal antibodies whose heavy-chain and light-chain sequences are both novel amino acid sequences and which can be used to prepare CD73 enzyme activity inhibitors and anti-tumor drugs.

3 Claims, 4 Drawing Sheets

Specification includes a Sequence Listing.

| | F2-2 | E1-B6 | 81-2-2 | 06-6 | 9-4 | Contbody |
|---|---|---|---|---|---|---|
| EC50 | 0.1094 | 0.2308 | 0.2392 | 0.2057 | 0.2113 | 0.1881 |

| | F2-2 | E1-B6 | 81-2-2 | 06-6 | 9-4 | Contbody |
|---|---|---|---|---|---|---|
| EC50 | 0.03971 | 0.1817 | 0.2133 | 0.1471 | 0.1754 | 0.1128 |

Data were presented as Mean±SD.

*,P<0.05, ,P<0.01, *,P<0.001, by one-way ANOVA

SEQUENCES OF ANTI-ECTO-5'-NUCLEOTIDASE ANTIBODIES

TECHNICAL FIELD

The present invention relates to genetically engineered antibodies and more particularly to the sequences of a plurality of anti-ecto-5'-nucleotidase antibodies.

DESCRIPTION OF RELATED ART

Ecto-5'-nucleotidase (hereinafter referred to as CD73 for short) is a multifunctional exonuclease.

While therapeutic CD73 monoclonal antibodies have been developed, a monoclonal antibody is secreted by a single hybridoma clone and can identify only one epitope (antigenic determinant). In fact, various monoclonal antibodies can be prepared according to the different antigenic epitopes of a biomacromolecule, and one antigenic epitope may even result in different monoclonal antibody sequences. As different sequences and target sites may give rise to higher drug efficacy, lower toxicity, or a wider anti-tumor spectrum, more anti-CD73 antibody sequences must be developed in order to solve more clinical problems.

BRIEF SUMMARY OF THE INVENTION

One objective of the present invention is to provide a variety of effective anti-CD73 antibody sequences that can be used to prepare drugs for treating tumor-related diseases.

The present invention involves immunizing mice with a human CD73 protein such that five anti-CD73 monoclonal antibodies were obtained. The heavy-chain and light-chain sequences of those monoclonal antibodies are novel sequences never reported in the prior art.

Four of the five anti-CD73 monoclonal antibodies obtained by the present invention can identify different antigenic epitopes from that identifiable by a prior art antibody.

The CD73 protein used in the present invention is a human CD73 protein whose expression was independently conducted by the applicant, and the mice used for the invention are BABL/c mice.

More specifically, the work conducted for the present invention as stated above was carried out by the following means:

A. The human CD73 protein was used as an antigen to immunize the BABL/c mice at a dose of 30 μg per mouse. Three weeks after the prime immunization, a boost immunization was performed with the same dose.

B. The titers of the antibodies in the serums of the immunized mice were determined by enzyme-linked immunosorbent assay (ELISA). Once an ideal titer was achieved, an immunological impact was given at a dose of 50 μg.

C. Spleen cells were extracted from the successfully immunized mice and were fused with SP2/0 cells. When the cells grew into clusters, the titers of the supernatants were determined. After three rounds of subcloning, positive monoclonal cell strains were obtained.

D. The monoclonal cell strains underwent expansion culture and were then introduced into the mice by intraperitoneal injection so as to produce ascitic fluids. The ascitic fluids were collected and purified to obtain the corresponding antibodies respectively.

E. The binding kinetics of the monoclonal antibodies were tested by the surface plasmon resonance (SPR) technique.

F. The inhibition effects of the monoclonal antibodies on the enzyme activity of CD73 were tested.

G. The tumor inhibition effects of the monoclonal antibodies on a transplanted tumor model were tested.

The five anti-CD73 monoclonal antibodies obtained by the present invention were respectively named F2-2, E1-B6, 81-2-2, 06-6, and 9-4. The molecular basis of the specificity of those antibodies lies mainly in the highly variable CDR1, CDR2, and CDR3 of the antibodies, wherein the CDRs are key areas that bind to an antigen.

The CDR1, CDR2, and CDR3 of the heavy chain and of the light chain of each of the five anti-CD73 monoclonal antibodies obtained by the present invention are polypeptides whose amino acid sequences are respectively defined as follows:

F2-2: SEQ ID NO: 1, SEQ ID NO: 2, and SEQ ID NO: 3; SEQ ID NO: 4, SEQ ID NO: 5, and SEQ ID NO: 6;

E1-B6: SEQ ID NO: 9, SEQ ID NO: 10, and SEQ ID NO: 11; SEQ ID NO: 12, SEQ ID NO: 13, and SEQ ID NO: 14;

81-2-2: SEQ ID NO: 17, SEQ ID NO: 18, and SEQ ID NO: 19; SEQ ID NO: 20, SEQ ID NO: 21, and SEQ ID NO: 22;

06-6: SEQ ID NO: 25, SEQ ID NO: 26, and SEQ ID NO: 27; SEQ ID NO: 28, SEQ ID NO: 29, and SEQ ID NO: 30; and 9-4: SEQ ID NO: 33, SEQ ID NO: 34, and SEQ ID NO: 35; SEQ ID NO: 36, SEQ ID NO: 37, and SEQ ID NO: 38.

As used herein, the term "monoclonal antibody" should be understood as covering any specific binding factor that has the desired specific binding domain and may refer to a monovalent or single-chain antibody, a double-chain antibody, a chimeric antibody, or a derivative, functional equivalent, or homolog of any of the foregoing antibodies, including an antibody fragment and any polypeptide that includes an antigen-binding domain One example of such monoclonal antibodies is immunoglobulin G (IgG) in any of its subclasses or subclass allotypes.

While the molecular basis of the specificity of an antibody lies mainly in the highly variable CDR1, CDR2, and CDR3 of the antibody, and the CDR sequences should therefore be preserved as much as possible to maintain the optimal binding properties, a change in individual amino acids may still allow the objective of the present invention to be achieved or may even lead to more optimal binding properties, provided that such a change in individual amino acids does not depart from the concept or inventive spirit of the invention.

The region of a heavy or light chain that does not form the highly variable CDR1, CDR2, or CDR3 is defined as a frame region. The frame regions can be substituted by other sequences under the condition that the three-dimensional structure required for binding is not affected.

The beneficial effects of the present invention are as follows:

The five anti-CD73 monoclonal antibodies produced in the present invention have been proved by experiments to have the following outstanding features:

1. They have high affinity toward human CD73 (see embodiment 2);

2. They can identify different epitopes from that identifiable by an existing anti-CD73 monoclonal antibody (see embodiment 3);

3. They are highly effective in inhibiting the enzyme activity of CD73, as demonstrated by biochemical-level and cell-level experiments (see embodiments 4); and 4. They can significantly inhibit the growth of transplanted tumors in mice reconstituted with human immune cells (see embodiment 5).

BRIEF DESCRIPTION OF THE SEVERAL VIEWS OF THE DRAWINGS

FIG. 4 and FIG. 5 shows the experimental results of embodiment 4 (inhibition effects of the antibodies F2-2, E1-B6, 81-2-2, 06-6, and 9-4 on the enzyme activity of CD73), in which FIG. 4 shows the results of a biochemical-level experiment, and FIG. 5 a cell (A459)-level experiment.

Figure 1:
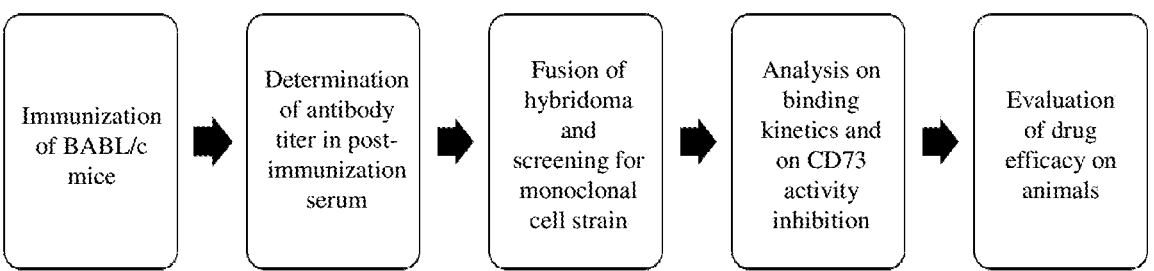
FIG. 1 shows the steps by which to obtain the five anti-CD73 monoclonal antibodies of the present invention.

F2-2, E1-B6, 81-2-2, 06-6, and 9-4 are the names of the five anti-CD73 monoclonal antibodies obtained by the present invention.

SEQUENCE INFORMATION

SEQ ID NO: 1, SEQ ID NO: 2, and SEQ ID NO: 3 are the CDR1, CDR2, and CDR3 of the heavy-chain variable region of the anti-CD73 monoclonal antibody F2-2 respectively;

SEQ ID NO: 4, SEQ ID NO: 5, and SEQ ID NO: 6 are the CDR1, CDR2, and CDR3 of the light-chain variable region of the anti-CD73 monoclonal antibody F2-2 respectively;

SEQ ID NO: 7 and SEQ ID NO: 8 are the heavy-chain and light-chain amino acid sequences of the anti-CD73 monoclonal antibody F2-2 respectively;

SEQ ID NO: 9, SEQ ID NO: 10, and SEQ ID NO: 11 are the CDR1, CDR2, and CDR3 of the heavy-chain variable region of the anti-CD73 monoclonal antibody E1-B6 respectively;

SEQ ID NO: 12, SEQ ID NO: 13, and SEQ ID NO: 14 are the CDR1, CDR2, and CDR3 of the light-chain variable region of the anti-CD73 monoclonal antibody E1-B6 respectively;

SEQ ID NO: 15 and SEQ ID NO: 16 are the heavy-chain and light-chain amino acid sequences of the anti-CD73 monoclonal antibody E1-B6 respectively;

SEQ ID NO: 17, SEQ ID NO: 18, and SEQ ID NO: 19 are the CDR1, CDR2, and CDR3 of the heavy-chain variable region of the anti-CD73 monoclonal antibody 81-2-2 respectively;

SEQ ID NO: 20, SEQ ID NO: 21, and SEQ ID NO: 22 are the CDR1, CDR2, and CDR3 of the light-chain variable region of the anti-CD73 monoclonal antibody 81-2-2 respectively;

SEQ ID NO: 23 and SEQ ID NO: 24 are the heavy-chain and light-chain amino acid sequences of the anti-CD73 monoclonal antibody 81-2-2 respectively;

SEQ ID NO: 25, SEQ ID NO: 26, and SEQ ID NO: 27 are the CDR1, CDR2, and CDR3 of the heavy-chain variable region of the heavy-chain variable region of the anti-CD73 monoclonal antibody 06-6 respectively;

SEQ ID NO: 28, SEQ ID NO: 29, and SEQ ID NO: 30 are the CDR1, CDR2, and CDR3 of the light-chain variable region of the anti-CD73 monoclonal antibody 06-6 respectively;

SEQ ID NO: 31 and SEQ ID NO: 32 are the heavy-chain and light-chain amino acid sequences of the anti-CD73 monoclonal antibody 06-6 respectively;

SEQ ID NO: 33, SEQ ID NO: 34, and SEQ ID NO: 35 are the CDR1, CDR2, and CDR3 of the heavy-chain variable region of the anti-CD73 monoclonal antibody 9-4 respectively;

SEQ ID NO: 36, SEQ ID NO: 37, and SEQ ID NO: 38 are the CDR1, CDR2, and CDR3 of the light-chain variable region of the anti-CD73 monoclonal antibody 9-4 respectively;

SEQ ID NO: 39 and SEQ ID NO: 40 are the heavy-chain and light-chain amino acid sequences of the anti-CD73 monoclonal antibody 9-4 respectively; and SEQ ID NO: 41 is the amino acid sequence of a CD73 protein whose construction and expression were independently conducted by the inventor of this application.

DETAILED DESCRIPTION OF THE INVENTION

The present invention provides the heavy chains and light-chain sequences of the following five specific anti-CD73 monoclonal antibodies. The monoclonal antibodies were respectively expressed by the corresponding monoclonal cell strains, which were obtained by screening hybridoma cells derived from BABL/c mice that had been immunized with a CD73 protein. The monoclonal antibodies are of the IgG type.

The antigen used in the following embodiments is a human CD73 protein whose expression was performed independently by the inventor, with the C terminus of the protein including a 6× His tag.

The immunologic adjuvant employed is the 5-week quick immunoadjuvant made by Beijing Biodragon Immunotechnologies Co., Ltd. A single boost immunization was conducted 21 days after the prime immunization. Cell fusion was carried out after immunological impact with the antigen was given once.

The fusion method employed is the electrofusion method. The electrofusion equipment used is model ECM2001 of BTX, with the fusion buffer being the cell fusion liquid provided by BTX.

Once the fused cells grew into clusters, antibody expression in the culture supernatant was tested by ELISA. The ELISA plate was coated with the CD73 protein or a His protein, wherein the His protein was used to prevent false positive holes due to anti-His.

Subcloning was performed on the positive holes by the limited dilution method. A total of three rounds of subcloning were performed, before positive monoclonal cell strains were obtained.

An ascitic fluid was prepared with each positive monoclonal cell strain and then purified to produce the corresponding monoclonal antibody. The monoclonal antibodies were subsequently subjected to an affinity test, an enzyme activity inhibition experiment, and an animal-based drug efficacy evaluation.

Embodiment 1: Immunization with an Antigen,
Cell Fusion, Screening for a Positive Clone, and
Preparation and Purification of an Ascitic Fluid
Antibody Purpose of the Experiment:

To prepare monoclonal antibodies with a human CD73 protein that serves as an antigen and whose expression is independently carried out.

Method of the Experiment:

Anti-human CD73 monoclonal antibodies were prepared by the hybridoma technology. More specifically, the preparation method is as follows:

Female BALB/c mice that were 4-6 weeks old were each immunized with 30 μg of the protein.

On the $21^{st}$ day after the prime immunization, a single boost immunization was given by the same method.

On the $35^{th}$ day after the prime immunization, blood was collected from the inner canthus, and serum was separated from the collected blood and subjected to an antibody titer test by ELISA.

When the antibody titer reached the required level, 50 μg of the CD73 protein was used as an antigen to make an immunological impact.

Three days after the immunological impact, spleen cells were taken to fuse with SP2/0 cells. Once cell clusters were formed, the anti-CD73 antibodies in the supernatant of the hybridomas were tested by ELISA.

Experimental Results:

After three rounds of subcloning, and by screening according to affinity and the enzyme activity inhabitation effect, five monoclonal cell strains in each of which an anti-CD73 antibody was highly expressed were obtained and were named F2-2, E1-B6, 81-2-2, 06-6, and 9-4 respectively. The monoclonal cells were expanded and then used to prepare ascetic fluids, which in turn were purified to obtain the antibodies for use in the subsequent affinity test, enzyme activity inhibition experiment, and animal-based drug efficacy test.

As stated below, the tests and experiments proved that all the five monoclonal antibodies have high affinity, are effective in inhibiting the enzyme activity of CD73, and as shown by the animal-based drug efficacy test, have desirable tumor inhibition effects.

Embodiment 2: Analysis of the Kinetics of the Five
Anti-CD73 Monoclonal Antibodies in Binding to
Recombinant Human CD73

Purpose of the Experiment:

To determine the binding-kinetics constants of each antibody with the Biacore T200 system.

Reagents and Method:

Mouse Antibody Capture Kit, which is a commercialized reagent kit, was purchased from GE. Anti-mouse Fc IgG was fixated on a CMS sensor chip by amine coupling in order to capture the antibody under test with the coupled anti-mouse Fc IgG. A series of human CD73 proteins having a predetermined concentration gradient were then injected, before the pH 1.7 glycine-HCl regeneration testing system that came with the reagent kit was used.

HBS-EP+ (10 mM HEPES; pH7.4, 150 mM NaCl; 3 mM EDTA; and 0.05% P20) was used as the running buffer, and the testing temperature was 25° C.

MEDI-9447, which is an anti-CD73 antibody developed by MedImmune LLC, was chosen for use as the reference antibody in the experiment and was obtained by synthesis according to the sequence disclosed in its patent specification (US2016/0194407 A1), followed by an expression and purification process.

The binding constant (Ka), dissociation rate constant (Kd), and equilibrium constant (KD) were calculated with the Biacore T200 evaluation software by combining the model fitting data at a 1:1 ratio.

Figure 2:
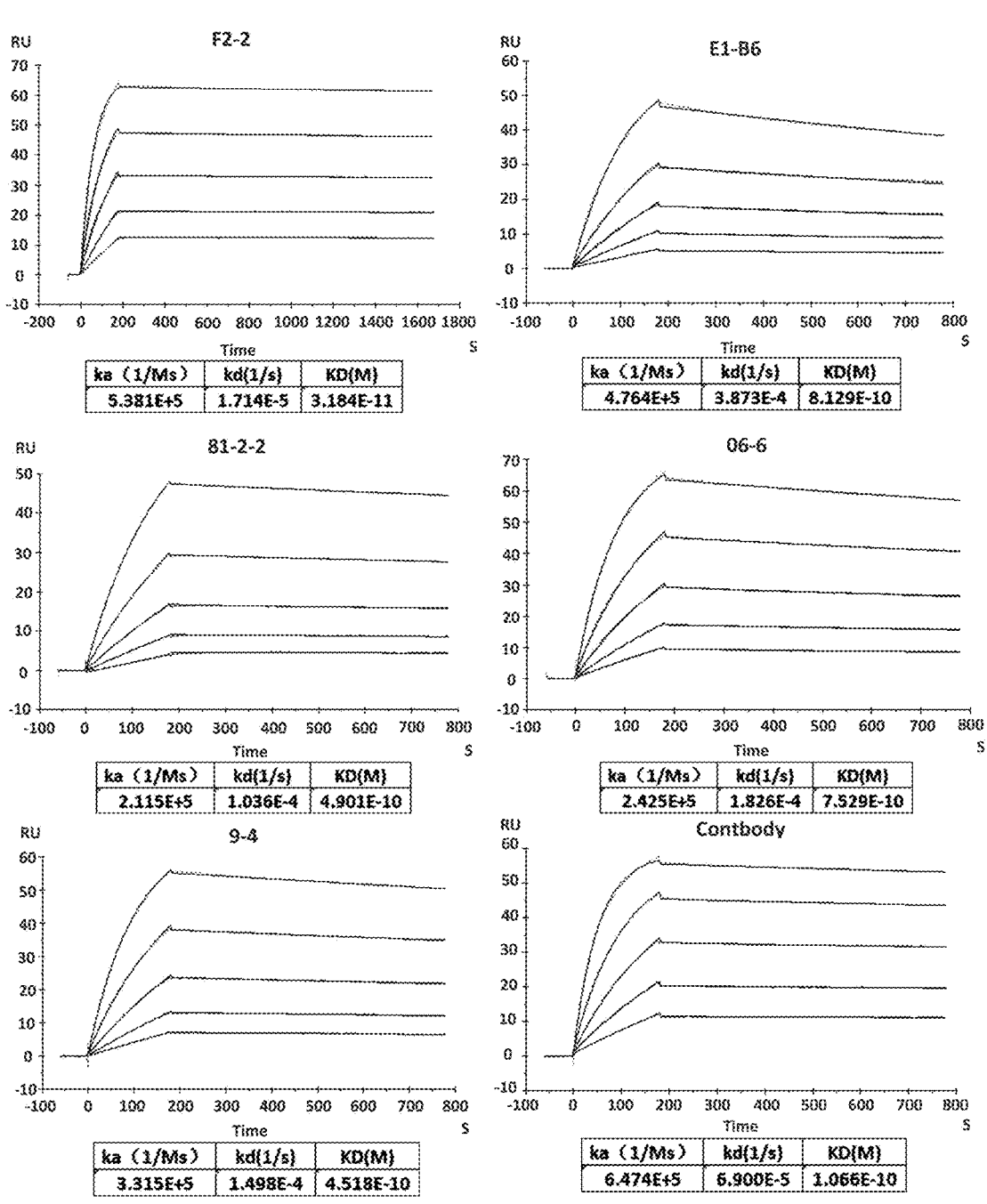
FIG. 2 shows the experimental results of embodiment 2 (affinity of the antibodies F2-2, E1-B6, 81-2-2, 06-6, and 9-4 toward human CD73), in which Ka, Kd, and KD are the binding constant, the dissociation constant, and the affinity constant respectively, and Contbody is MEDI-9447.

Experimental Results:

The experimental results, or more particularly the affinity data of each antibody, are shown in FIG. 2 and the following table:

| Antibody | Ka (1/Ms) | Kd (1/s) | KD (M) |
|---|---|---|---|
| F2-2 | $5.381 \times 10^5$ | $1.714 \times 10^{-5}$ | $3.184 \times 10^{-11}$ |
| E1-B6 | $4.764 \times 10^5$ | $3.873 \times 10^{-5}$ | $8.129 \times 10^{-10}$ |
| 81-2-2 | $2.115 \times 10^5$ | $1.036 \times 10^{-4}$ | $4.901 \times 10^{-10}$ |
| 06-6 | $2.425 \times 10^5$ | $1.826 \times 10^{-4}$ | $7.529 \times 10^{-10}$ |
| 9-4 | $3.315 \times 10^5$ | $1.498 \times 10^{-4}$ | $4.518 \times 10^{-10}$ |
| Reference | $6.474 \times 10^5$ | $6.900 \times 10^{-5}$ | $1.066 \times 10^{-10}$ |

According to the experimental results, all the five anti-CD73 monoclonal antibodies had high affinity toward the recombinant human CD73, and F2-2 had higher affinity than the other four antibodies. Moreover, the antibody F2-2 had higher affinity than MEDI-9447, whereas the other four antibodies had slightly lower affinity than MEDI-9447.

Conclusion of the Experiment:

All the five anti-CD73 monoclonal antibodies obtained by the present invention had high affinity toward human CD73.

Embodiment 3: Analysis of the Antigenic Epitopes
of the Five Anti-CD73 MONOCLONAL
ANTIBODIES Purpose of the Experiment:

To analyze the difference between the antigenic epitopes of the antibodies.

Reagents and Method:

The difference between the antigenic epitopes of the antibodies was analyzed with the Biacore T200 system.

Mouse Antibody Capture Kit, which is a commercialized reagent kit, was purchased from GE. Anti-mouse Fc IgG was fixated on a CM5 sensor chip by amine coupling in order to capture the first antibody with the coupled anti-mouse Fc IgG. After that, 100 μg/mL mouse IgG was used to close the redundant sites, and then CD73 and the second antibody were sequentially injected. The sensing results were plotted into a graph in order to analyze the difference between the antigenic epitopes respectively identified by the antibodies.

MEDI-9447 was chosen for use as the reference antibody in the experiment.

Figure 3:
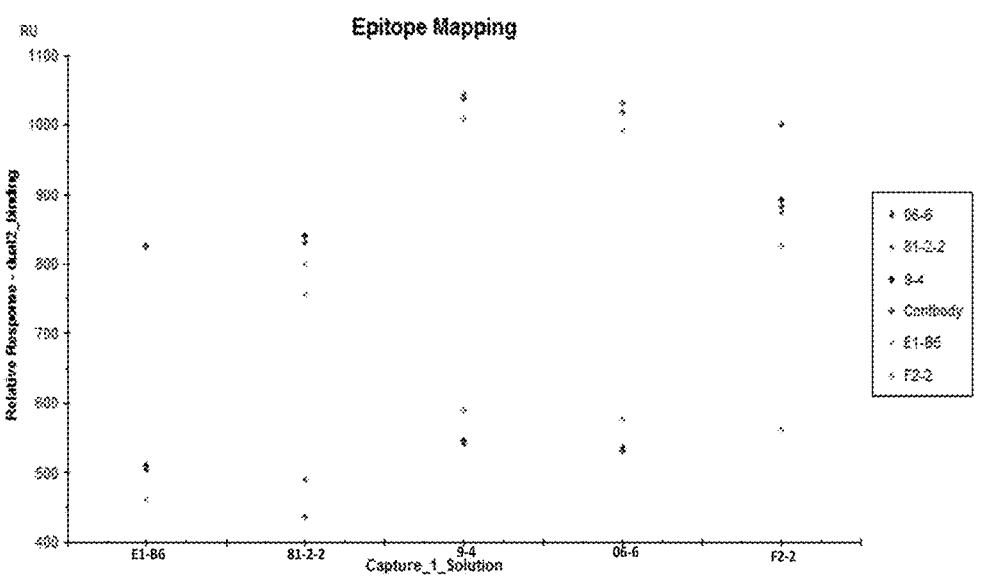
FIG. 3 shows the experimental results of embodiment 3 (analysis of the antibody epitopes of the antibodies F2-2, E1-B6, 81-2-2, 06-6, and 9-4), in which the epitope identified by each of E1-B6, 81-2-2, 9-4, 06-4, and F2-2 is sequentially plotted, in the foregoing order of the antibodies, against the rest of the antibodies plus Contbody, which is MEDI-9447.

Experimental Results:

The experimental results are detailed in FIG. 3.

The epitopes of the antibodies are summarized in the following table according to the analysis result:

| Identified epitope | | Antibody | |
|---|---|---|---|
| Epitope 1 | F2-2 | | |
| Epitope 2 | E1-B6 | 06-6 | 9-4 |
| Epitope 3 | 81-2-2 | Reference | |

The epitope mapping result shows that the antibody F2-2 identified a distinct epitope from those identified by the rest of the five antibodies of the present invention, whereas the antibodies E1-B6, 06-6, and 9-4 identified the same epitope; and that four of the five antibodies identified a different epitope from that identified by MEDI-9447, whereas 81-2-2 identified the same antigenic epitope as MEDI-9447. Now that the CDR amino acid sequences of 81-2-2 are different from those of MEDI-9447, 81-2-2 is still a novel antibody different from MEDI-9447.

Conclusion of the Experiment:

Of the five anti-CD73 monoclonal antibodies obtained by the present invention, four antibodies identified a different antigenic epitope from that identified by the existing anti-CD73 monoclonal antibody.

Embodiment 4: Inhibition of the Enzyme Activity of CD73 by the Five Antibodies Purpose of the Experiment:

To perform a biochemical-level test and a cell-level test on the ability of the antibodies F2-2, E1-B6, 81-2-2, 06-6, and 9-4 to inhibit the enzyme activity of CD73.

Method of the Experiment:

1. Biochemical Method

The antibodies F2-2, E1-B6, 81-2-2, 06-6, 9-4, and MEDI-9447 were added separately to the holes of a blank 96-hole plate at an appropriate concentration gradient, and each hole was subsequently added with the CD73 protein until the final CD73 protein concentration was 0.25 μg/mL. After incubation at 37° C. for 15 min, AMP and ATP were added separately until their final concentrations were 500 μmol/L and 100 μmol/L respectively. After further incubation at 37° C. for 30 min, each hole was added with the same volume of Cell titer Glo.

The signal values of each hole were determined with a microplate reader by the chemiluminescence method, and the data obtained was subjected to further calculation and processing.

2. Cell-Based Method

The antibodies F2-2, E1-B6, 81-2-2, 06-6, 9-4, and MEDI-9447 were added separately to the holes of a 96-hole plate at an appropriate concentration gradient. A549 cells were digested, resuspended, and counted, and then each hole was inoculated with the A549 cells at a density of $1\times10^5$ cells/hole. After incubation in a carbon dioxide incubator for 15 min, each hole was added with AMP until the final AMP concentration reached 500 μmol/L. After further incubation in the carbon dioxide incubator for 24 h, the 96-hole plate was taken out of the incubator and centrifuged at 1000 rpm for 5 min, and 50 μL of supernatant was taken from each hole and added to the corresponding hole of a new blank 96-hole plate. Each hole of the new plate was then added with an ATP solution until the finial ATP concentration was 100 μmol/L, and each hole was subsequently added with the same volume of Cell titer Glo.

The signal values of each hole were determined with a microplate reader by the chemiluminescence method, and the data obtained was subjected to further calculation and processing.

Figure 4:
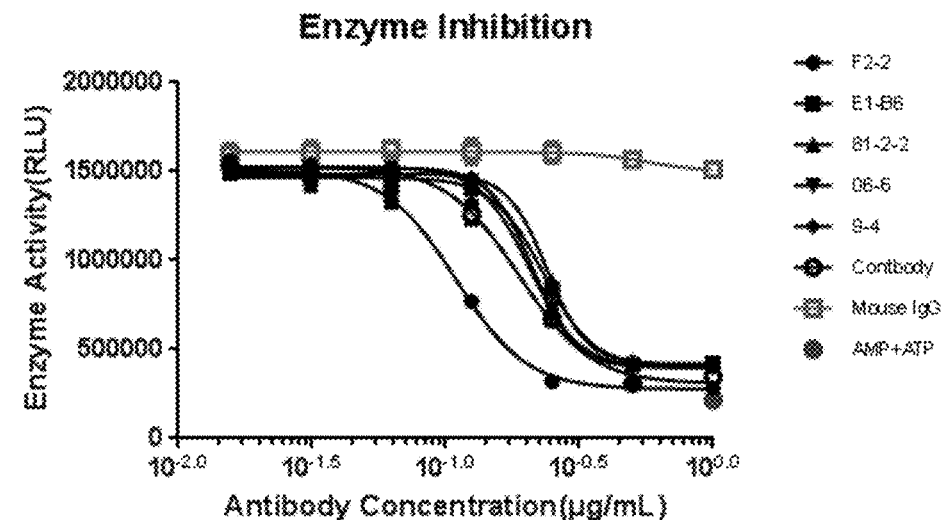
Figure 5:
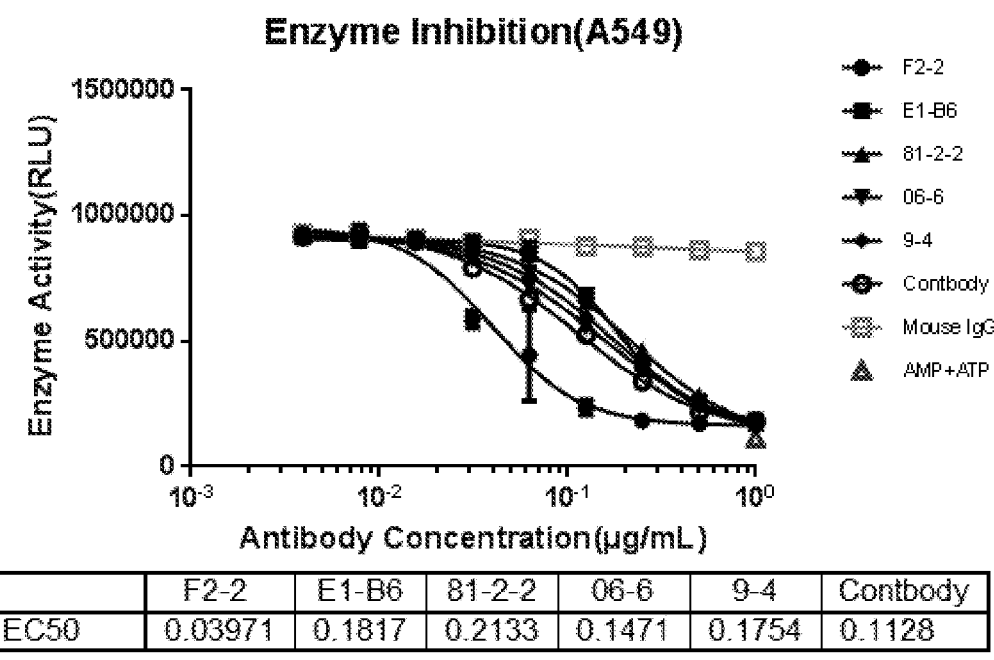

Experimental Results:

See FIG. 4 and FIG. 5.

The inhibition effects of the antibodies on the enzyme activity of CD73 are summarized in the following table, in which the reference antibody is MEDI-9447:

| | | Antibody | | | | | |
|---|---|---|---|---|---|---|---|
| | | F2-2 | E1-B6 | 81-2-2 | 06-6 | 9-4 | Reference |
| $EC_{50}$ (μg/mL) | Biochemical level | 0.1094 | 0.2318 | 0.2392 | 0.2057 | 0.2113 | 0.1881 |
| | Cell level | 0.03971 | 0.1817 | 0.2133 | 0.1471 | 0.1754 | 0.1128 |

In the five monoclonal antibodies of the present invention, F2-2 exhibited a better CD73 enzyme activity inhibition effect than the other four antibodies and MEDI-9447 on both the biochemical level and the cell level, and E1-B6, 81-2-2, 06-6, and 9-4 had a slightly weaker CD73 enzyme activity inhibition effect than MEDI-9447.

Conclusion of the Experiment:

Both the biochemical-level and cell-level experiments show that the five anti-CD73 monoclonal antibodies obtained by the present invention were highly effective in inhibiting the enzyme activity of CD73.

Embodiment 5: Evaluation of the Drug Efficacy of the Five Antibodies on Animals Purpose of the Experiment:

To test the inhibition effects of the five antibodies on the growth of tumor cells by conducting an in vivo experiment.

Method of the Experiment:

Ninety B-NDG mice were used. The mice received adaptive feeding for at least one week.

A549 cells were cultured. Subculturing was performed every other day. The cells were eventually collected, and phosphate-buffered saline (PBS) was added to adjust the cell density to $5\times10^7$/mL. Each mouse was inoculated with 0.1 mL of the cell suspension by subcutaneous injection into the right shoulder.

About 10 days after the inoculation, mice with a tumor volume ranging from 20 to 30 $mm^3$ were divided into 7 groups, each including 10 mice.

Peripheral blood mononuclear cells (PBMCs) were resuscitated on the day the mice were grouped, and PBS was added to the PBMCs to adjust the cell density to 25 million/mL. Each mouse was intravenously injected with 200 μL (5 million) of PBMCs and then medicated through intravenous injection. After that, the tumor volumes were measured twice a week. The drugs were administered at the frequency of Q3D for a total of 10 times.

A tumor growth curve was plotted for each group, with the vertical axis representing tumor volume, and the horizontal axis representing the drug administration time. One-way ANOVA analysis was performed on each medicated group and the control group in order to compare, and find the differences between, the groups.

Figure 6:
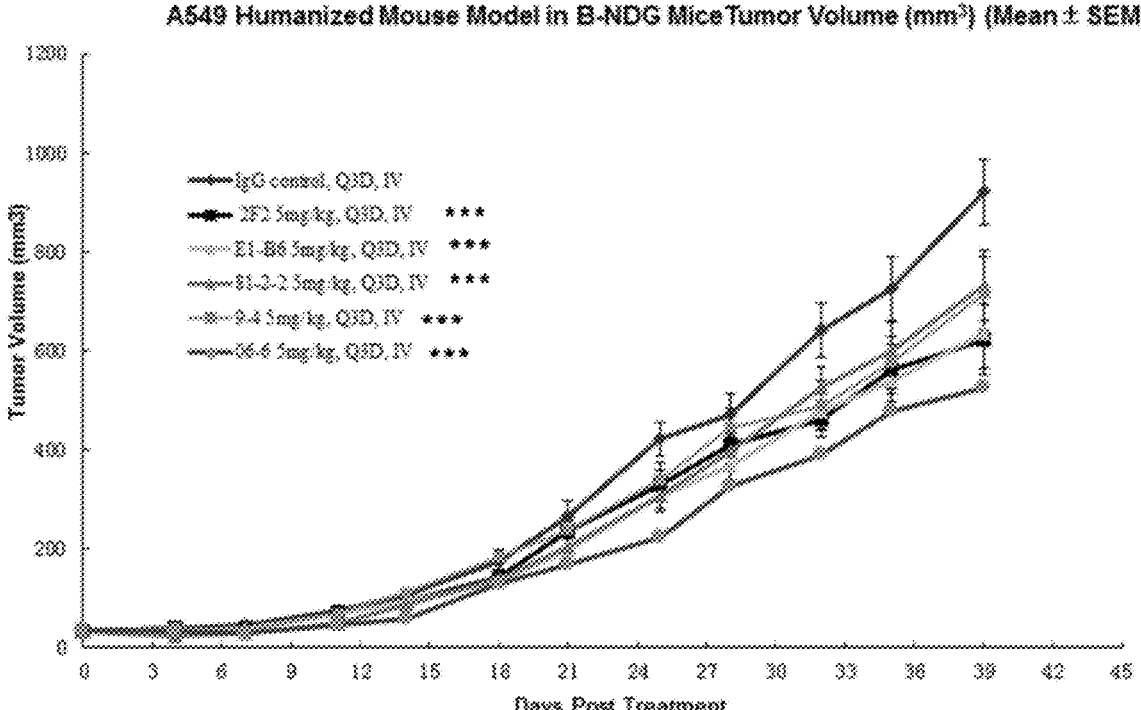
FIG. 6 shows the experimental results of embodiment 5 (drug efficacy of the antibodies F2-2, E1-B6, 81-2-2, 06-6, and 9-4 on animals)

Experimental results: See FIG. 6. The experimental results show that, compared with the control-group IgG, all the antibodies F2-2, E1-B6, 81-2-2, 06-6, and 9-4 had significant inhibition effects on the growth of tumor cells. In particular, 81-2-2 and 9-4 had similar effects, F2-2 and E1-B6 had similar effects, and 06-6 had the highest drug efficacy.

Conclusion of the Experiment:

All the five anti-CD73 monoclonal antibodies of the present invention had significant inhibition effects on the growth of tumor cells.

The invention claimed is:

1. An anti-ecto-5'-nucleotidase (CD73) monoclonal antibody, selected from the group consisting of:

(a) a heavy chain variable region comprising CDR1, CDR2, and CDR3 amino acid sequences of SEQ ID NO: 1, SEQ ID NO: 2, and SEQ ID NO: 3, respectively; and a light chain variable region comprising CDR1, CDR2, and CDR3 amino acid sequences of SEQ ID NO: 4, SEQ ID NO: 5, and SEQ ID NO: 6, respectively;

(b) a heavy chain variable region comprising CDR1, CDR2, and CDR3 amino acid sequences of SEQ ID NO: 9, SEQ ID NO: 10, and SEQ ID NO: 11, respectively; and a light chain variable region comprising CDR1, CDR2, and CDR3 amino acid sequences of SEQ ID NO: 12, SEQ ID NO: 13, and SEQ ID NO: 14, respectively;

(c) a heavy chain variable region comprising CDR1, CDR2, and CDR3 amino acid sequences of SEQ ID NO: 17, SEQ ID NO: 18, and SEQ ID NO: 19, respectively; and a light chain variable region comprising CDR1, CDR2, and CDR3 amino acid sequences of SEQ ID NO: 20, SEQ ID NO: 21, and SEQ ID NO: 22, respectively;

(d) a heavy chain variable region comprising CDR1, CDR2, and CDR3 amino acid sequences of SEQ ID NO: 25, SEQ ID NO: 26, and SEQ ID NO: 27, respectively; and a light chain variable region comprising CDR1, CDR2, and CDR3 amino acid sequences of SEQ ID NO: 28, SEQ ID NO: 29, and SEQ ID NO: 30, respectively; and (e) a heavy chain variable region comprising CDR1, CDR2, and CDR3 amino acid sequences of SEQ ID NO: 33, SEQ ID NO: 34, and SEQ ID NO: 35, respectively; and a light chain variable region comprising CDR1, CDR2, and CDR3 amino acid sequences of SEQ ID NO: 36, SEQ ID NO: 37, and SEQ ID NO: 38, respectively.

2. An anti-tumor drug comprising the monoclonal antibody of claim 1.

3. A CD73 enzyme activity inhibitor comprising the monoclonal antibody of claim 1.

\* \* \* \* \*

SEQUENCE LISTING

```
<160> NUMBER OF SEQ ID NOS: 41

<210> SEQ ID NO 1
<211> LENGTH: 9
<212> TYPE: PRT
<213> ORGANISM: Mus musculus

<400> SEQUENCE: 1

Gly His Ser Ile Thr Ser Asp Tyr Val
1               5

<210> SEQ ID NO 2
<211> LENGTH: 7
<212> TYPE: PRT
<213> ORGANISM: Mus musculus

<400> SEQUENCE: 2

Ile Ser Tyr Ser Gly Ile Ile
1               5

<210> SEQ ID NO 3
<211> LENGTH: 10
<212> TYPE: PRT
<213> ORGANISM: Mus musculus

<400> SEQUENCE: 3

Ala Gly Asp Glu Tyr Phe Trp Phe Ala Tyr
1               5                   10

<210> SEQ ID NO 4
<211> LENGTH: 6
<212> TYPE: PRT
<213> ORGANISM: Mus musculus

<400> SEQUENCE: 4

Gln Asp Ile Lys Ser Tyr
1               5

<210> SEQ ID NO 5
<211> LENGTH: 3
<212> TYPE: PRT
<213> ORGANISM: Mus musculus

<400> SEQUENCE: 5

Tyr Ala Thr
1

<210> SEQ ID NO 6
<211> LENGTH: 9
<212> TYPE: PRT
<213> ORGANISM: Mus musculus
```

-continued

<400> SEQUENCE: 6

Leu Gln His Gly Glu Ser Pro Tyr Thr
1               5

<210> SEQ ID NO 7
<211> LENGTH: 116
<212> TYPE: PRT
<213> ORGANISM: Mus musculus

<400> SEQUENCE: 7

Val Gln Leu Gln Glu Ser Gly Pro Gly Leu Val Lys Pro Ser Gln Ser
1               5                   10                  15

Leu Ser Leu Thr Cys Thr Val Thr Gly His Ser Ile Thr Ser Asp Tyr
            20                  25                  30

Val Trp Asn Trp Ile Arg Gln Phe Pro Gly Asn Lys Leu Glu Trp Met
            35                  40                  45

Gly Tyr Ile Ser Tyr Ser Gly Ile Ile Lys Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Gly Asp Glu Tyr Phe Trp Phe Ala Tyr Trp Gly Gln Gly Thr Thr Val
                100                 105                 110

Thr Val Ser Ser
            115

<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
            35                  40                  45

Tyr Tyr Ala Thr Asn Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Tyr
                85                  90                  95

Thr Phe Gly Gly Gly Thr Lys Leu Glu Ile Lys
                100                 105

<210> SEQ ID NO 9
<211> LENGTH: 8
<212> TYPE: PRT
<213> ORGANISM: Mus musculus

<400> SEQUENCE: 9

Gly Tyr Thr Phe Thr Asp Tyr Tyr
1               5

```
<210> SEQ ID NO 10
<211> LENGTH: 8
<212> TYPE: PRT
<213> ORGANISM: Mus musculus

<400> SEQUENCE: 10

Thr Tyr Pro Gly Asn Gly Asn Thr
1               5

<210> SEQ ID NO 11
<211> LENGTH: 14
<212> TYPE: PRT
<213> ORGANISM: Mus musculus

<400> SEQUENCE: 11

Ala Arg Gly Thr Tyr Tyr Gly Ser Ser Glu Tyr Phe Asp Tyr
1               5                   10

<210> SEQ ID NO 12
<211> LENGTH: 6
<212> TYPE: PRT
<213> ORGANISM: Mus musculus

<400> SEQUENCE: 12

Gln Asn Val Gly Thr Ala
1               5

<210> SEQ ID NO 13
<211> LENGTH: 3
<212> TYPE: PRT
<213> ORGANISM: Mus musculus

<400> SEQUENCE: 13

Ser Ala Ser
1

<210> SEQ ID NO 14
<211> LENGTH: 9
<212> TYPE: PRT
<213> ORGANISM: Mus musculus

<400> SEQUENCE: 14

Gln Gln Tyr Ser Ser Tyr Ile Phe Thr
1               5

<210> SEQ ID NO 15
<211> LENGTH: 120
<212> TYPE: PRT
<213> ORGANISM: Mus musculus

<400> SEQUENCE: 15

Val Lys Leu Gln Glu Ser Gly Ala Glu Leu Ala Arg Pro Gly Ala Ser
1               5                   10                  15

Val Lys Leu Ser Cys Lys Ala Ser Gly Tyr Thr Phe Thr Asp Tyr Tyr
            20                  25                  30

Ile Asn Trp Val Lys Gln Arg Thr Gly Gln Gly Leu Glu Trp Ile Gly
        35                  40                  45

Glu Thr Tyr Pro Gly Asn Gly Asn Thr Tyr Tyr His Glu Lys Phe Lys
    50                  55                  60

Gly Lys Ala Thr Leu Thr Ala Asp Arg Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95
```

-continued

```
Arg Gly Thr Tyr Tyr Gly Ser Ser Glu Tyr Phe Asp Tyr Trp Gly Gln
            100                 105                 110

Gly Thr Thr Val Thr Val Ser Ser
        115                 120

<210> SEQ ID NO 16
<211> LENGTH: 107
<212> TYPE: PRT
<213> ORGANISM: Mus musculus

<400> SEQUENCE: 16

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Arg Pro Gly Gln Ser Pro Lys Leu Leu Ile
            35                  40                  45

Tyr Ser Ala Ser Asn Arg Asn Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Ile Phe
                85                  90                  95

Thr Phe Gly Ser Gly Thr Lys Leu Glu Ile Asn
            100                 105

<210> SEQ ID NO 17
<211> LENGTH: 8
<212> TYPE: PRT
<213> ORGANISM: Mus musculus

<400> SEQUENCE: 17

Gly Tyr Thr Phe Thr Ser Tyr Trp
1               5

<210> SEQ ID NO 18
<211> LENGTH: 8
<212> TYPE: PRT
<213> ORGANISM: Mus musculus

<400> SEQUENCE: 18

Ile Asn Pro Ser Asn Gly Arg Thr
1               5

<210> SEQ ID NO 19
<211> LENGTH: 12
<212> TYPE: PRT
<213> ORGANISM: Mus musculus

<400> SEQUENCE: 19

Ala Arg Arg Gly Thr Ser Gly Asn Phe Phe Asp Tyr
1               5                   10

<210> SEQ ID NO 20
<211> LENGTH: 6
<212> TYPE: PRT
<213> ORGANISM: Mus musculus

<400> SEQUENCE: 20

Gln Asp Ile Asn Thr Tyr
1               5
```

-continued

```
<210> SEQ ID NO 21
<211> LENGTH: 3
<212> TYPE: PRT
<213> ORGANISM: Mus musculus

<400> SEQUENCE: 21

Arg Ala Asn
1

<210> SEQ ID NO 22
<211> LENGTH: 9
<212> TYPE: PRT
<213> ORGANISM: Mus musculus

<400> SEQUENCE: 22

Leu Gln Phe Asp Glu Phe Pro Tyr Thr
1               5

<210> SEQ ID NO 23
<211> LENGTH: 119
<212> TYPE: PRT
<213> ORGANISM: Mus musculus

<400> SEQUENCE: 23

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Thr Ser Gly Asn Phe Phe Asp Tyr Trp Gly Gln Gly
            100                 105                 110

Thr Thr Leu Thr Val Ser Ser
        115

<210> SEQ ID NO 24
<211> LENGTH: 107
<212> TYPE: PRT
<213> ORGANISM: Mus musculus

<400> SEQUENCE: 24

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80
```

-continued

```
Glu Asp Met Gly Ile Tyr Tyr Cys Leu Gln Phe Asp Glu Phe Pro Tyr
                85                  90                  95

Thr Phe Gly Gly Gly Thr Lys Leu Glu Ile Lys
            100                 105

<210> SEQ ID NO 25
<211> LENGTH: 8
<212> TYPE: PRT
<213> ORGANISM: Mus musculus

<400> SEQUENCE: 25

Gly Tyr Thr Phe Ala Asp Tyr Phe
1               5

<210> SEQ ID NO 26
<211> LENGTH: 8
<212> TYPE: PRT
<213> ORGANISM: Mus musculus

<400> SEQUENCE: 26

Ile Tyr Pro Gly Tyr Val Asn Ile
1               5

<210> SEQ ID NO 27
<211> LENGTH: 12
<212> TYPE: PRT
<213> ORGANISM: Mus musculus

<400> SEQUENCE: 27

Ala Arg Gly Glu Asp Tyr Asp Ser Ala Met Asp Tyr
1               5                   10

<210> SEQ ID NO 28
<211> LENGTH: 11
<212> TYPE: PRT
<213> ORGANISM: Mus musculus

<400> SEQUENCE: 28

Gln Ser Leu Val His Ser Asn Gly Asn Thr Tyr
1               5                   10

<210> SEQ ID NO 29
<211> LENGTH: 3
<212> TYPE: PRT
<213> ORGANISM: Mus musculus

<400> SEQUENCE: 29

Lys Val Ser
1

<210> SEQ ID NO 30
<211> LENGTH: 10
<212> TYPE: PRT
<213> ORGANISM: Mus musculus

<400> SEQUENCE: 30

Ser Gln Ser Thr His Val Pro Pro Trp Thr
1               5                   10

<210> SEQ ID NO 31
<211> LENGTH: 119
<212> TYPE: PRT
<213> ORGANISM: Mus musculus
```

<400> SEQUENCE: 31

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Ala Asp Tyr
            20                  25                  30

Phe Met His Trp Val Arg Leu Arg Pro Gly Gln Gly Leu Glu Trp Ile
        35                  40                  45

Gly Trp Ile Tyr Pro Gly Tyr Val Asn Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Glu Asp Tyr Asp Ser Ala Met Asp Tyr Trp Gly Gln Gly
            100                 105                 110

Thr Ser Val Thr Val Ser Ser
        115

<210> SEQ ID NO 32
<211> LENGTH: 113
<212> TYPE: PRT
<213> ORGANISM: Mus musculus

<400> SEQUENCE: 32

Gly Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 33
<211> LENGTH: 10
<212> TYPE: PRT
<213> ORGANISM: Mus musculus

<400> SEQUENCE: 33

Gly Phe Ser Leu Ser Thr Ser Gly Met Gly
1               5                   10

<210> SEQ ID NO 34
<211> LENGTH: 7
<212> TYPE: PRT
<213> ORGANISM: Mus musculus

<400> SEQUENCE: 34

Ile Tyr Trp Asp Asp Asp Lys
1               5

```
<210> SEQ ID NO 35
<211> LENGTH: 12
<212> TYPE: PRT
<213> ORGANISM: Mus musculus

<400> SEQUENCE: 35

Ala Arg Arg Arg Ser Leu Asp Gly Trp Phe Ala Tyr
1               5                   10

<210> SEQ ID NO 36
<211> LENGTH: 6
<212> TYPE: PRT
<213> ORGANISM: Mus musculus

<400> SEQUENCE: 36

Gly Asn Ile His Asn Tyr
1               5

<210> SEQ ID NO 37
<211> LENGTH: 3
<212> TYPE: PRT
<213> ORGANISM: Mus musculus

<400> SEQUENCE: 37

Asn Thr Gln
1

<210> SEQ ID NO 38
<211> LENGTH: 9
<212> TYPE: PRT
<213> ORGANISM: Mus musculus

<400> SEQUENCE: 38

Gln His Phe Trp Asp Ser Pro Trp Thr
1               5

<210> SEQ ID NO 39
<211> LENGTH: 120
<212> TYPE: PRT
<213> ORGANISM: Mus musculus

<400> SEQUENCE: 39

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Asp Lys Arg Tyr Asn Pro Ser
        50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Arg Ser Leu Asp Gly Trp Phe Ala Tyr Trp Gly Gln
            100                 105                 110

Gly Thr Leu Val Thr Val Ser Ala
            115                 120

<210> SEQ ID NO 40
<211> LENGTH: 107
```

```
<212> TYPE: PRT
<213> ORGANISM: Mus musculus

<400> SEQUENCE: 40

Asp Ile Gln Met Thr Gln Ser Pro Ala Ala Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Thr Gln Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Phe Tyr Cys Gln His Phe Trp Asp Ser Pro Trp
                85                  90                  95

Thr Phe Gly Gly Gly Thr Lys Met Glu Ile Lys
            100                 105

<210> SEQ ID NO 41
<211> LENGTH: 527
<212> TYPE: PRT
<213> ORGANISM: Artificial Sequence
<220> FEATURE:
<223> OTHER INFORMATION: Synthetic

<400> SEQUENCE: 41

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220
```

```
Gly Asn Pro Pro Ser Lys Glu Val Pro Ala Gly Lys Tyr Pro Phe Ile
225             230             235             240

Val Thr Ser Asp Asp Gly Arg Lys Val Pro Val Val Gln Ala Tyr Ala
            245             250             255

Phe Gly Lys Tyr Leu Gly Tyr Leu Lys Ile Glu Phe Asp Glu Arg Gly
            260             265             270

Asn Val Ile Ser Ser His Gly Asn Pro Ile Leu Leu Asn Ser Ser Ile
            275             280             285

Pro Glu Asp Pro Ser Ile Lys Ala Asp Ile Asn Lys Trp Arg Ile Lys
        290             295             300

Leu Asp Asn Tyr Ser Thr Gln Glu Leu Gly Lys Thr Ile Val Tyr Leu
305             310             315             320

Asp Gly Ser Ser Gln Ser Cys Arg Phe Arg Glu Cys Asn Met Gly Asn
            325             330             335

Leu Ile Cys Asp Ala Met Ile Asn Asn Asn Leu Arg His Thr Asp Glu
            340             345             350

Met Phe Trp Asn His Val Ser Met Cys Ile Leu Asn Gly Gly Gly Ile
            355             360             365

Arg Ser Pro Ile Asp Glu Arg Asn Asn Gly Thr Ile Thr Trp Glu Asn
        370             375             380

Leu Ala Ala Val Leu Pro Phe Gly Gly Thr Phe Asp Leu Val Gln Leu
385             390             395             400

Lys Gly Ser Thr Leu Lys Lys Ala Phe Glu His Ser Val His Arg Tyr
            405             410             415

Gly Gln Ser Thr Gly Glu Phe Leu Gln Val Gly Gly Ile His Val Val
            420             425             430

Tyr Asp Leu Ser Arg Lys Pro Gly Asp Arg Val Val Lys Leu Asp Val
            435             440             445

Leu Cys Thr Lys Cys Arg Val Pro Ser Tyr Asp Pro Leu Lys Met Asp
        450             455             460

Glu Val Tyr Lys Val Ile Leu Pro Asn Phe Leu Ala Asn Gly Gly Asp
465             470             475             480

Gly Phe Gln Met Ile Lys Asp Glu Leu Leu Arg His Asp Ser Gly Asp
            485             490             495

Gln Asp Ile Asn Val Val Ser Thr Tyr Ile Ser Lys Met Lys Val Ile
            500             505             510

Tyr Pro Ala Val Glu Gly Arg Ile Lys His His His His His His
        515             520             525
```